(12) United States Patent
Paulucci et al.

(10) Patent No.: US 11,583,480 B2
(45) Date of Patent: Feb. 21, 2023

(54) SUNSCREEN COMPOSITION WITH A HIGH UV FILTER LOAD

(71) Applicant: L'OREAL, Paris (FR)

(72) Inventors: Jennifer Lynn Paulucci, Manalapan, NJ (US); Jaimie Mecca, Clifton, NJ (US); Patricia Brieva, Manalapan, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/552,827

(22) Filed: Aug. 27, 2019

(65) Prior Publication Data

US 2021/0059911 A1    Mar. 4, 2021

(51) Int. Cl.
| | | |
|---|---|---|
| A61K 8/06 | (2006.01) | |
| A61K 8/81 | (2006.01) | |
| A61K 8/37 | (2006.01) | |
| A61K 8/40 | (2006.01) | |
| A61K 8/49 | (2006.01) | |
| A61Q 17/04 | (2006.01) | |
| A61K 8/86 | (2006.01) | |

(52) U.S. Cl.
CPC ............... *A61K 8/062* (2013.01); *A61K 8/37* (2013.01); *A61K 8/375* (2013.01); *A61K 8/40* (2013.01); *A61K 8/498* (2013.01); *A61K 8/8147* (2013.01); *A61K 8/86* (2013.01); *A61Q 17/04* (2013.01)

(58) Field of Classification Search
CPC .................................................... A61Q 17/04
See application file for complete search history.

(56) References Cited

U.S. PATENT DOCUMENTS

| | | | |
|---|---|---|---|
| 4,427,836 | A | 1/1984 | Kowalski et al. |
| 4,469,825 | A | 9/1984 | Kowalski et al. |
| 4,594,363 | A | 6/1986 | Blankenship et al. |
| 4,677,003 | A | 6/1987 | Redlich et al. |
| 4,920,160 | A | 4/1990 | Chip et al. |
| 4,970,241 | A | 11/1990 | Kowalski et al. |
| 5,116,604 | A | 5/1992 | Fogel et al. |
| 5,156,911 | A | 10/1992 | Stewart |
| 5,157,084 | A | 10/1992 | Lee et al. |
| 5,476,648 | A | 12/1995 | Fogel |
| 5,505,948 | A | 4/1996 | Rapaport |
| 5,620,682 | A | 4/1997 | Fogel |
| 5,624,663 | A | 4/1997 | Deflandre et al. |
| 5,663,213 | A | 9/1997 | Jones et al. |
| 6,210,658 | B1 | 4/2001 | Bonda |
| 8,557,227 | B2 | 10/2013 | Simonnet et al. |
| 9,050,475 | B2 | 6/2015 | Nurse et al. |
| 2009/0009807 | A1 | 1/2009 | Sugi |
| 2009/0189090 | A1* | 7/2009 | Meyer ............... A61K 8/678 424/59 |
| 2012/0015016 | A1 | 1/2012 | Galdi et al. |
| 2013/0028853 | A1 | 1/2013 | Nurse et al. |
| 2013/0078200 | A1 | 3/2013 | Daly et al. |
| 2013/0101515 | A1 | 4/2013 | Meyer et al. |
| 2013/0129650 | A1 | 5/2013 | Simonnet et al. |
| 2014/0170090 | A1 | 6/2014 | Thaggard |
| 2015/0202139 | A1 | 7/2015 | Friedman |
| 2015/0306017 | A1* | 10/2015 | Fanizza ............... A61K 8/0279 424/401 |
| 2017/0312199 | A1 | 11/2017 | Shah et al. |

FOREIGN PATENT DOCUMENTS

| | | | | |
|---|---|---|---|---|
| CN | 102387780 | A * | 3/2012 | ............... A61K 8/72 |
| EP | 331421 | A2 | 9/1989 | |
| EP | 267726 | B1 | 5/1993 | |
| EP | 0967200 | B1 | 4/2002 | |
| EP | 1092421 | B1 | 3/2007 | |
| EP | 2252253 | B1 * | 5/2013 | ........... A61K 8/8147 |
| EP | 2152685 | B1 * | 1/2017 | ............ A61Q 19/02 |
| EP | 2874710 | B1 | 10/2017 | |
| WO | 1996/019180 | A1 | 6/1995 | |
| WO | 2014/012699 | A2 | 1/2014 | |
| WO | 2014/114888 | A2 | 7/2014 | |
| WO | 2014/140312 | A1 | 9/2014 | |
| WO | 2014/161490 | A1 | 10/2014 | |
| WO | 2015/118038 | A1 | 8/2015 | |
| WO | 2015/124233 | A1 | 8/2015 | |
| WO | WO-2017053959 | A1 * | 3/2017 | ........... A61K 8/0241 |

OTHER PUBLICATIONS

DiNardo et al., "Dermatological and environmental toxicological impact of the sunscreen ingredient oxybenzone/benzophenone-3", J Cosmet Dermatol. 2018;17:15-19. (Year: 2018).*
"Span and Tween", Croda, Aug. 2010. (Year: 2010).*
"Tego Care 165", Evonik Industries, Apr. 2008. (Year: 2008).*
Oresajo, Christian et al., Complementary effects of antioxidants and sunscreens in reducing UV-induced skin damage as demonstrated by skin biomaker expression, Journal of Cosmetic and Laser Therapy, vol. 12, p. 157-162 (2010).
Prospector, Oxynex ST Liquid Merck KGaA Personal Care Cosmetics, accessed: Nov. 18, 2017.
Sunspheres, Dow Personal Care, American Chemistry Council (ACC), Feb. 2006.
Xue, Faith, "The Secret world of SPF enhancers", Byrdie, p. 1-4, (2018).

* cited by examiner

*Primary Examiner* — Gina C Justice
(74) *Attorney, Agent, or Firm* — Laetitia Leproust; Robert Klemz

(57) ABSTRACT

An oil-in-water composition is provided. The composition includes an oil-in-water wherein the emulsion includes a) one or more antioxidants, b) one or more SPF boosters, c) one or more acrylate-based polymer capable of stabilizing the composition, d) one or more organic UV filters, e) one or more thickeners, f) one or more film formers; and g) one or more emulsifiers. The oil-in-water composition is provided in which the composition is essentially free of oxybenzone.

14 Claims, No Drawings

SUNSCREEN COMPOSITION WITH A HIGH UV FILTER LOAD

FIELD OF THE DISCLOSURE

The instant disclosure relates to sunscreen compositions with a high UV filter load.

BACKGROUND

Skin acts as a natural barrier between the internal and the external environment and therefore plays an important role in vital biological functions such as protection against ultraviolet damage. Skin, however, is delicate and is easily damaged. For example, the negative effects of extended exposure to sunlight are well-known; for example, prolonged exposure causes sunburns. When skin is exposed to UV light having a wavelength of from about 290 nm to about 400 nm, long term damage can lead to serious conditions such as skin-aging.

As described in more detail below, the inventors of the instant disclosure discovered compositions and methods that protect the skin from UV damages. The components of the compositions interact to improve the SPF of the UV filters and provide water resistance. Thus, the compositions are useful for a variety of cosmetic compositions.

Accordingly, it is desirable to produce a stable formulation comprising an oil-in-water dispersion which is highly water resistant, maintains high levels of sunscreen protection, provides provide uniform skin coverage and is aesthetically pleasing, i.e., does not feel oily or 50 greasy.

SUMMARY OF THE DISCLOSURE

The instant disclosure relates to sunscreen compositions which provide a high degree of sun protection and are aesthetically pleasing when applied to skin. The sunscreen compositions in the form of an oil-in-water emulsion typically include:
  a) from about 0.1 to about 5 wt. % of one or more antioxidants,
  b) from about 0.5 to about 7 wt. % of one or more SPF boosters,
  c) one or more acrylate-based polymer capable of stabilizing the composition,
  d) one or more organic UV filters,
  e) one or more thickeners;
  f) one or more film formers;
  g) one or more emulsifiers; and
  wherein the weight percentages are based on the total weight of the oil-in-water composition.

The sunscreen compositions are particularly unique in that they exhibit a very high degree of sun protection without containing any oxybenzone. In some embodiments, the composition of the instant disclosure is essentially free of oxybenzone. In one embodiment, the oil-in-water composition is less than about 0.1 wt. % oxybenzone based on the total weight of the oil-in-water composition.

In some embodiments, the oil-in-water composition has an SPF of at least about 80.

In some embodiments, the one or more antioxidants is selected from diethylhexyl syringylidene malonate, tocopherol, and mixture thereof. In one embodiment, the one or more antioxidants is present in an amount from about 0.5 to about 2 wt. % based on the total weight of the oil-in-water composition.

In some embodiments, the one or more SPF boosters is selected from styrene/acrylate copolymers, (co)polymers of (meth)acrylic acid, (meth)acrylates, poly(meth)acrylates and mixture thereof. In one embodiment, the one or more SPF boosters is present in an amount from about 0.8 to about 3 wt. % based on the total weight of the oil-in-water composition.

In some embodiments, the one or more acrylate-based polymers is present in an amount from about 0.1 to about 10 wt. % based on the total weight of the oil-in-water composition. In some embodiments, the one or more acrylate-based polymers is capable of stabilizing the composition. In one or more embodiments, the one or more acrylate-based polymer is a member selected from the group consisting of polyacrylate-1 crosspolymer, carbomer, acrylates/C10-30 alkyl acrylate crosspolymer, acrylates/acrylamide copolymer and acrylate copolymer, and mixture thereof.

In some embodiments, the one or more organic UV filters is selected from the group consisting of a para-aminobenzoic acid derivatives, ansalicylic derivatives a cinnamic derivative, a benzophenone or an aminobenzophenone, an anthranillic derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, merocyanine, an amalonitrile or malonate diphenyl butadiene derivative, a chalcone, and a mixture thereof. In some embodiments, the one or more organic UV filters is a mixture of two or more UV filters. In one embodiments, the one or more organic UV filters is a mixture of three or more UV filters. In some embodiments the one or more organic UV filters is present in an amount from about 10 to about 40 wt. % based on the total weight of the oil-in-water composition.

In some embodiments, the one or more UV filters is present in an amount from about 20 to about 35 wt. % based on the total weight of the oil-in-water composition.

In some embodiments, the one or more thickeners is selected from the group C10 to C30 alkyl (meth)acrylate homopolymer, a poly(stearyl acrylate) or poly(behenyl acrylate) homopolymer, a poly(stearyl acrylate)homopolymer; and mixture thereof. In one or more embodiments, the one or more thickeners is present in an amount from about 0.1 to 10 wt. % based on the total weight of the oil-in-water composition.

In some embodiments, the film former is present in an amount from about 0.1 to about 5 wt. % based on the total weight of the oil-in-water composition. In one or more embodiments, the film former is selected from Acrylates/Dimethicone copolymer, polycacrylate-21 (and) acrylates/dimethylaminoethylmethacrylate copolymer, polyurethanes, polysaccharides, polyvinylpyrrolidone, acrylates, and a mixture thereof.

In some embodiments, the one or more emulsifiers comprises a non-ionic emulsifier. In some embodiments, the nonionic emulsifier is a compound selected from the group consisting of a polyol ester, a glycerol ether, an oxyethylenated and/or oxypropylenated ether, and/or an ethylene glycol polymer, and mixture thereof. In one embodiment, the nonionic emulsifier is a polyol ester and/or an ethylene glycol polymer. In one embodiments, the nonionic emulsifier of is a combination of glyceryl stearate and PEG-100 stearate. In some embodiments, the one or more emulsifiers is present from about 0.1 to about 10 wt. % based on the total weight of the oil-in-water composition.

In some embodiments, the compositions disclosed in the instant disclosure is water resistant.

In some embodiments, the oil-in-water composition may comprise:
  a) from about 0.1 to about 5 wt. % of one or more antioxidants,
  b) from about 0.5 to about 7 wt. % of one or more SPF boosters,
  c) from about 0.1 to about 10 wt. % of one or more acrylate-based polymers capable of stabilizing the composition,
  d) from about 15 to about 40 wt. % of one or more organic UV filters,
  e) from about 0.1 to about 10 wt. % of one or more thickeners selected from the group C10 to C30 alkyl (meth)acrylate homopolymer, a poly(stearyl acrylate) or poly(behenyl acrylate) homopolymer, a poly(stearyl acrylate)homopolymer; and mixture thereof,
  f) from about 0.1 to about 5 wt. % of one or more film formers;
  g) from about 0.1 to about 10 wt. % of one or more emulsifiers; and
  wherein the weight percentages are based on the total weight of the oil-in-water composition.

The instant disclosure also relates to methods for protecting skin or hair from UV radiation comprising applying an effective amount of the oil-in-water composition disclosed in the instant case to the skin or hair.

The oil-in-water compositions of the instant disclosure provide unexpected high level of SPF without oxybenzone, with a very high water resistance and very stable.

Without being bound by theory or mechanism, it is suggested that the stability of the oil-in-water composition disclosed in the instant case is due to the combination of presence of the one or more acrylate-based polymers, the one or more thickeners and the one or more emulsifiers.

It is to be understood that both the foregoing general description and the following detailed description are exemplary and explanatory only, and are not restrictive of the invention.

DETAILED DESCRIPTION OF THE DISCLOSURE

The oil-in-water compositions of the instant disclosure, in their broadest sense, typically include the following:
  a) from about 0.1 to about 5 wt. % of one or more antioxidants,
  b) from about 0.5 to about 7 wt. % of one or more SPF boosters,
  c) one or more acrylate-based polymers capable stabilizing the composition,
  d) one or more organic UV filters,
  e) one or more thickeners;
  f) one or more film formers;
  g) one or more emulsifiers; and
  wherein the weight percentages are based on the total weight of the oil-in-water composition.

The composition according to embodiments of the instant disclosure may be free or essentially free of oxybenzone.

As used herein, "essentially free" indicates that oxybenzone is present only in de minimus amounts as an impurity in other ingredients, and the oxybenzone does not materially affect the properties of the composition. In yet another embodiment, the composition is free of oxybenzone.

As used herein, "free" indicates that no reliably measurable oxybenzone is present in the composition.

As used herein, the term "stable" means the emulsion remains intact without phase separation, color and/or odor change over the stability monitoring period and the water-soluble active ingredients remain solubilized in the water phase without crystallization or precipitation out of the emulsion.

Antioxidants

In some cases, the one or more antioxidants includes diethylhexyl syringylidene malonate, tocopherol, and mixture thereof. In some instances, the total amount of the one or more antioxidants in the composition may be from about 0.5 to about 2 wt. % based on the total weight of the oil-in-water composition.

The one of more antioxidants may include any suitable composition, including, but not limited to, diethylhexyl syringlidenemalonate (INCI name) (formula I)

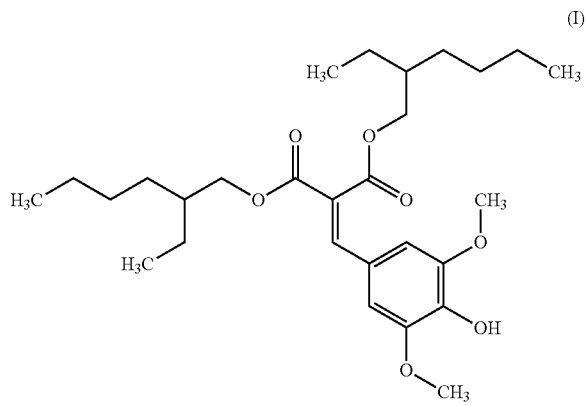 [SMILES: CCCCC(CC)COC(=O)C(=Cc1cc(OC)c(O)c(OC)c1)C(=O)OCC(CC)CCCC]

Diethylhexyl syringylidenmalonate is commercially available from Merck KgaA under the trade name Oxynex® ST.

The one or more antioxidants include any antioxidant suitable for use in cosmetic formulations, including, but not limited to, vitamin C, resveratrol, tannic acid, polyphenols, amino acids and derivatives thereof, imidazoles, peptides such as carnosine and derivatives, carotenoids, carotenes (such as α-carotene, β-carotene, and lycopene), α-hydroxy acids (such as citric acid, lactic acid, or malic acid), tocopherols and derivatives (such as Vitamin E), Phenylethyl resorcinol, resorcinol derivates, vitamin A, co-enzyme Q10, bioflavonoids, glutathione, plant extracts (such as rosemary extract, olive leaf extracts), and green tea extracts.

Furthermore, the total amount of the one or more antioxidants can vary but is typically from about 0.5, 0.6, 0.7, 0.8, 0.9, 1.0, 1.1, 1.2 to about 1.2, 1.3, 1.4, 1.5, 1.6, 1.7, 1.8, 1.9, or 2 wt. % based on the total weight of the oil-in-water composition.

SPF Booster

As used herein, the term "SPF booster" refers to a material which increases the UV absorption of another material when the two are intermixed in a composition by refracting UV radiation, thereby increasing the effective path length of the UV radiation through the composition.

The one or more SPF boosters may include any suitable material, including, but not limited to a plurality of light refracting bodies. The plurality of light refracting bodies may have any composition and conformation. In one embodiment, the conformation of the light refracting bodies is a hollow sphere. In a further embodiment, the hollow sphere is filled with a substance having a refractive index which is different from the material from which the hollow sphere itself is made, yielding a structure which refracts UV radiation. In another embodiment, the composition of the light refracting bodies, specifically the material from which the hollow sphere itself is made, includes a styrene-acrylate copolymer composition. In a further embodiment, the composition of the light refracting bodies is a latex.

According to one particular embodiment of the instant disclosure, the light refracting bodies are constituted of a copolymer of styrene and (meth)acrylic acid or one of its alkyl esters under the INCI name Styrene/Acrylates Copolymer, such as the product sold under the tradename SUNSPHERES® powder by the company Dow chemical, which is an aqueous dispersion containing about 86% of Styrene/Acrylates Copolymer in a mixture of about 11% of PEG-8 Laurate, about 2.5% of water, and about 0.5% of Sodium Dodecylbenzenesulfonate.

In one embodiment, the SPF boosters suitable for use with the instant disclosure have a particle size which ranges generally from about 100 to about 380 nm, alternatively from about 150 to about 375 nm, alternatively from about 190 to about 350 nm, alternatively from about 251 to about 325 nm, the particle size being a volume-average particle size measured by a photon correlation spectrometer such as a Brookhaven BI-90 photon correlation spectrophotometer.

The light refracting bodies may possess any suitable void fraction, including, but not limited to, a void fraction of 0.1% to 50%, alternatively 5% to 50%. In some instances, the void fractions may be determined by comparing the volume occupied by the light refracting bodies after having been compacted from a diluted dispersion in a centrifuge, relative to the volume of non-void particles of the same composition.

Light refracting bodies which are hollow latex particles, according to one embodiment of the invention, are obtained from particles comprising at least one polymer for the core and at least one polymer for the shell. The core polymer and the shell polymer may be obtained from a single polymerization step or from a sequence of polymerization steps. Such hollow latex particles may be provided as part of an aqueous dispersion that is stabilized with at least one emulsifier.

The hollow latex particles may be prepared by any suitable method, including, but not limited to the conventional techniques of emulsion polymerization. Such processes are described especially in U.S. Pat. Nos. 4,427,836, 4,469,825, 4,594,363, 4,677,003, 4,920,160, and 4,970,241 or by the conventional techniques of polymerization that are described in the following patents and patent applications: EP267726, EP331421, U.S. Pat. Nos. 490,229, and 5,157,084. The above patents are incorporated by reference in their entirety.

The monomers used for the shell of the latex particles may include one or more unsaturated nonionic ethylenic units. Optionally one or more monoethylenically unsaturated monomers containing at least one carboxylic acid group may be polymerized in the shell. In one embodiment, the monomers constituting the shell are selected such that they exhibit a glass transition temperature (Tg) which is sufficiently high to withstand the void of the hollow latex particle. The glass transition temperature may be greater than 50° C., alternatively greater than 60° C., alternatively greater than 70° C. The glass temperature (Tg) may be determined by differential scanning calorimetry.

The monomers used in the emulsion polymerization for the core polymer of the hollow latex particles of the invention may include one or more monoethylenically unsaturated monomers containing at least one carboxylic acid group. The core may include at least 5% by weight of monoethylenically unsaturated monomers containing at least one carboxylic acid group, relative to the total weight of the core monomers. The core polymer may, for example, be obtained by emulsion homopolymerization of the monoethylenically unsaturated monomer containing at least one acid group or by copolymerization of two or three monoethylenically unsaturated monomers containing at least one acid group. In one embodiment, the monoethylenically unsaturated monomer containing at least one acid group is copolymerized with one or more ethylenically unsaturated nonionic monomers.

The core polymer or the shell polymer may contain from 0.1% to 20% by weight, and, in some embodiments, from 0.1% to 3% by weight, of polyethylenically unsaturated monomers, such as ethylene glycol di(meth)acrylate, allyl (meth)acrylate, 1,3-butanediol di(meth)acrylate, diethylene glycol di(meth)acrylate, trimethylolpropane tri(meth)acrylate, or divinylbenzene, relative to the total weight of the core monomers. Alternatively, the core polymer or the shell polymer may optionally contain from 0.1% to 60% by weight of butadiene, relative to the total weight of the core monomers.

The monoethylenically unsaturated monomers containing at least one carboxylic acid group may include, by way of example, acrylic acid, methacrylic acid, acryloyloxypropionic acid, (meth)acryloyloxypropionic acid, itaconic acid, aconitic acid, maleic acid or maleic anhydride, fumaric acid, crotonic acid, monomethyl maleate, monomethyl fumarate, and monomethyl itaconate.

In one embodiment, the monomer is selected from acrylic acid and methacrylic acid. The monoethylenically unsaturated nonionic monomers may include, by way of example, styrene, vinyl toluene, vinyl acetate, vinyl chloride, vinylidene chloride, acrylonitrile, (meth)acrylamide, C1-C20 alkyl esters of (meth)acrylic acid, and (C3-C20) alkenyl esters of (meth)acrylic acid, such as methyl (meth)acrylate, ethyl (meth)acrylate, butyl (meth)acrylate, 2-ethylhexyl (meth)acrylate, benzyl (meth)acrylate, lauryl (meth)acrylate, oleyl (meth)acrylate, palmityl (meth)acrylate, and stearyl (meth)acrylate. As used herein, "(meth)acrylic" denotes the general expression encompassing both methacrylic or acrylic, and "(meth)acrylate" denotes the general expression encompassing both methacrylate or acrylate.

The void of the core of the latex particles may be produced by swelling the core with a swelling agent comprising one or more volatile compounds. The agent penetrates the shell in order to swell the core. The volatile components of the swelling agent may be subsequently removed by drying the latex particles, thus creating a void within the particles. The agent is, in some embodiments, an aqueous base. Mention may be made, for example, of ammonia, ammonium hydroxide, alkali metal hydroxides, such as sodium hydroxide, and volatile amines, such as trimethylamine or triethylamine.

The hollow latex particles may be introduced into the composition with the swelling agent. In such an embodiment, the volatile compounds are removed when the composition is dried. The hollow latex particles may also be added to the composition after the volatile compounds of the swelling agent have been removed.

In one embodiment, the hollow latex particles are those described in U.S. Pat. No. 5,663,213 and patent application EP1092421, which are hereby incorporated by reference in their entirety.

In another embodiment, the hollow spheres of the light refracting bodies of the SPF booster include glass microspheres. Glass microspheres used in the compositions may be essentially homogeneous and essentially uniform in sphericity. The glass microspheres may have any suitable mean particle size, including, but not limited to, a mean particle size of between about 5 µm and 70 µm, alternatively from about 10 µm to 20 µm. Glass microspheres may include hollow microspheres of calcium aluminum borosilicate (commercially available from Presperse Inc. under the tradename LUXSIL®), sodium borosilicate particulates (commercially available from PQ Corporation under the tradename Q-CEL 570), and calcium/sodium borosilicate hollow microspheres (commercially available from 3M under the tradenames ES 22 and 1K), calcium/sodium borosilicate microspheres (commercially available from 3M's under the tradename Scotchlite™ K20 product).

In yet another embodiment, the light refracting bodies of the SPF booster include porous silica in the form of microparticles, in particular, spherical microparticles. The spherical microparticles of porous silica may have any suitable mean particle size, including, but not limited to, a mean particle size ranging from 0.5 µm to 20 µm, alternatively from 3 µm to 15 µm. Further, the microparticles may have any suitable specific surface, including, but not limited to, a specific surface ranging from 50 m2/g to 1,000 m2/g, alternatively from 150 m2/g to 800 m2/g. Also, the microparticles may have any suitable specific pore volume, including, but not limited to, a specific pore volume ranging from 0.5 ml/g to 5 ml/g, alternatively from 1 ml/g to 2 ml/g. By way of example, the porous silica spherical microparticles may include commercial products such as Silica Beads SB 150 from Myoshi, Sunsphere H-51 from Asahi Glass, Sunsil 130 from Sunjin, Spherica P-1500 from Ikeda Corporation, and Sylosphere from Fuji Silysia.

In one embodiment, the SPF booster includes at least one material selected from the group consisting of (co)polymers of (meth)acrylic acid, (meth)acrylates, and/or styrene, glass, and silica. In another embodiment, the SPF booster includes at least two materials selected from the group consisting of (co)polymers of (meth)acrylic acid, (meth)acrylates, and/or styrene, glass, and silica. In yet another embodiment, the SPF booster includes a (co)polymers of (meth)acrylic acid, (meth)acrylates, and/or styrene, glass, and silica. The (co) polymers of (meth)acrylic acid, (meth)acrylates, and/or styrene, may be made of poly(meth)acrylates, such as PMMA, a copolymer of (meth)acrylic acid and (meth)acrylates, and a copolymer of (meth)acrylic acid, (meth)acrylates, and styrene.

In some embodiments, the one or more SPF boosters is selected from styrene/acrylate copolymers, (co)polymers of (meth)acrylic acid, (meth)acrylates, poly(meth)acrylates and mixture thereof. In one embodiment, the one or more SPF boosters is present in an amount from about 0.8 to about 3 wt. % based on the total weight of the oil-in-water composition.

The total amount of SPF boosters in the oil-in-water compositions can vary but is typically from about 0.8, 0.9, 1.0, 1.2, 1.3, 1.4, 1.5, 1.6, 1.7, 1.8 to about 1.8, 1.9, 2.0, 2.1, 2.2, 2.3, 2.4, 2.5, 2.6, 2.7, 2.8, 2.9, or 3 wt. % based on the total weight of the oil-in-water composition.

Acrylates-Based Polymers

An acrylate-based polymer capable of thickening the composition is helpful to provide stabilization of the composition, and thus yielding favorable properties to the oil-in-water sunscreen compositions.

The acrylate-based polymer can be a copolymer or a crosspolymer. One type of an acrylate-based polymer is known by the INCI name "acrylates/C10-30 alkyl acrylate crosspolymer". Additional examples of the acrylate-based polymer include, but not limited to, polyacrylate-1 crosspolymer, carbomer, acrylates/acrylamide copolymer and acrylate copolymer.

According to an embodiment, the one or more acrylate-based polymers capable of stabilizing the composition is an acrylates/C10-30 alkyl acrylate crosspolymer.

According to an embodiment, the total amount of acrylate-based polymer ranges from about 0.1, 0.5, 2, 2.5, 3, 3.5, 4, 4.5, 5, 5.5 to about 5.5, 6.0, 6.5, 7.0, 7.5, 8.0, 8.5, 9.0, 9.5, or 10 wt. % based on the total weight of the oil-in-water composition.

UV Filters

The composition may include any suitable amount of one or more UV filters. In one embodiment, the composition includes about 15 wt % to about 35 wt % UV filter, alternatively about 20 wt % to about 30 wt %, alternatively about 25 wt %.

The one or more UV filters may include any suitable UV filter or UV filter system, including, but not limited to, solid organic lipsoluble UV filters, such as, but not limited to, butyl methoxydibenzoylmethane, and ethylhexyl trazone, liposoluble organic UV filters, such as, but not limited to, cinnamate compounds, anthranilates, salicylate compounds, dibenzoylmethane compounds, such as avobenzone, camphor compounds, β,β-diphénylacrylate compounds, triazine compounds, benzotriazole compounds, benzalmalonate compounds (particularly those cited in U.S. Pat. No. 5,624,663), imidazoline compounds, p-aminobenzoate compounds (PABA), benzoxazole compounds (as described in patent applications EP0832642, EP1027883, EP1300137, and DE10162844), UV-filter polymers and UV-filter silicones (as described in patent application WO-93/04665), α-alkyl-styrène dimers (as described in patent application DE19855649), 4,4-diarylbutadiens (as described in patent applications EP0967200, DE19746654, DE19755649, EP-A-1008586, EP1133980, and EP133981), mérocyanine (as described in U.S. Pat. No. 4,195,999, WO2004/006878, WO2008/090066, WO2011113718, WO2009027258, and the documents IP COM JOURNAL No 000179675D published on Feb. 23, 2009, IP COM JOURNAL No 000182396D published on Apr. 29, 2009, IP COM JOURNAL No 000189542D published on Nov. 12, 2009, IP COM Journal No IPCOM000011179D published on Mar. 4, 2004), and their mixtures. The above documents are incorporated by reference in their entirety.

By way of non-limiting example, at least one UV filter or UV filter system may include (listed by INCI name): dibenzoylmethane compounds such as butylmethoxydibenzoylmethane (for example, as sold under the trade name Parsol 1789® by DSM Nutritional Products, Inc.) and isopropyldibenzoylmethane; para-aminobenzoic compounds such as ethyl PABA, ethyl dihydroxypropyl PABA, ethylhexyl diméthyl PABA (sold under the name ESCALOL 507® by ISP), and glyceryl PABA; salicylic derivatives such as homosalate (sold under the commercial name Eusolex HMS by Rona/EM Industries) and ethylhexyl salicylate (sold under the commercial name NEO HELIOPAN OS by SYMRISE); cinnamic derivatives such as ethylhexyl methoxycinnamate (sold under the commercial name PARSOL MCX by DSM NUTRITIONAL PRODUCTS.), isopropyl methoxy cinnamate, isoamyl methoxy cinnamate (sold under the commercial name NEO HELIOPAN E 1000 by SYMRISE), and cinoxate, diisopropyl methylcinnamate; derivatives of β,β-diphenylacrylate such as octocrylene (sold under the commercial name UVINUL N539 by BASF) and etocrylene (sold under the commercial name UVINUL N35 by BASF); and hexyl 2-(4-diethylamino-2-hydroxybenzoyl) benzoate (sold under the commercial name UVINUL A Plus or in the form of a mixture with octylmethoxycinnamate under the commercial name UVINUL A+B by BASF); benzylidenecamphor derivatives such as 3-Benzylidene camphor (manufactured under the commercial name MEXORYL SD by CHIMEX), 4-Methylbenzylidene camphor (sold under the commercial name EUSOLEX 6300 by MERC), and polyacrylamidomethyl benzylidene camphor (manufactured under the commercial name MEXORYL SW by CHIMEX); phenyl benzotriazole derivatives such as drometrizole trisiloxane (sold under the commercial name Silatrizole by RHODIA CHIMIE); triazine derivatives such as bis-ethylhexyloxyphenol methoxyphenyl triazine (sold under the commercial name TINOSORB S by BASF), ethylhexyl triazone (sold under the commercial name UVINUL T150 by BASF), diethylhexyl butamido triazone (sold under the commercial name UVASORB HEB by SIGMA 3V), 2,4,6-tris(4'-amino benzalmalonate de dinéopentyle)-s-triazine, 2,4,6-tris-(diisobutyle-4'-amino benzalmalonate)-s-triazine, and 2,4-bis (dinéopentyle-4'-aminobenzalmalonate)-6-(4'-aminobenzoate de n-butyle)-s-triazine; triazine silicones substituted by two aminobenzoates groups such 2,4-bis-(n-butyl 4'-aminobenzalmalonate)-6-[(3-{1,3,3,3-tetramethyl-1-[(trimethyl-silyloxy]-disiloxanyl}propyl)amino]-s-triazine (and others as described in the patent EP0841341); anthranilic derivatives such as menthyl anthranilate (sold under the commercial name NEO HELIOPAN MA by SYMRISE), imidazoline derivatives such as ethylhexyl dimethoxybenzylidene dioxoimidazoline propionate; benzalmalonate derivatives such as di-neopentyl 4'-methoxybenzalmalonate and polyorganosiloxane with benzalmalonate functions such as Polysilicone-15 (sold under the commercial name PARSOL SLX by DSM NUTRITIONAL PRODUCTS); derivatives of 4,4- diarylbutadiene such as 1,1-dicarboxy (2,2'-diméthyl-propyl)-4,4-diphénylbutadiène; benzoxazole derivatives such as 2,4-bis-[5-1(diméthylpropyl)benzoxazol-2-yl-(4-phenyl)-imino]-6-(2-ethylhexyl)-imino-1,3,5-triazine (sold under the commercial name Uvasorb K2A by Sigma 3V); lipophilic merocyanine derivatives such as Octyl-5-N,N-diethylamino-2-phenysulfonyl-2,4-pentadienoate; terephthalylidene dicamphor sulfonic acid (Sold under the commercial name Mexoryl SX by CHIMEX; and drometrizole trisiloxane (Sold under the commercial name Mexoryl XL by RHODIA).

In one embodiment, one or more UV-A filter is avobenzone and one or more one UV-B filter includes, consists essentially of or consists of octisalate, octocrylene, and homosalate. In another embodiment, the UV-A filter is avobenzone and the UV-B filter includes, consists essentially of or consists of at least two of octisalate, octocrylene, and homosalate. In still another embodiment, the UV filter system including the UV-A and the UV-B filters includes, consists essentially of or consists of each of avobenzone, octisalate, octocrylene, and homosalate.

Thickeners

The thickeners used in the present disclosure can be selected from semi-crystalline or crystalline polymers and/or semi-crystalline or crystalline waxes.

(I) Semi-Crystalline or Crystalline Polymer

The semi-crystalline or crystalline polymer is preferably a semi-crystalline polymer. The term "semi-crystalline polymer" means polymers comprising a crystallizable portion, a crystallizable pendent and/or end chain or a crystallizable block in the backbone and/or at the ends, and an amorphous portion in the backbone, and having a first-order reversible temperature of change of phase, in particular of melting (solid-liquid transition). When the crystallizable portion is in the form of a crystallizable block of the polymer backbone, the amorphous portion of the polymer is in the form of an amorphous block; the semi-crystalline polymer is, in this case, a block copolymer, for example of the diblock, triblock or multiblock type, comprising at least one crystallizable block and at least one amorphous block. The term "block" generally means at least five identical repeating units. The crystallizable block(s) are then of different chemical nature from the amorphous block(s).

The semi-crystalline polymer according to the present disclosure has a melting point of greater than or equal to 30° C., preferably ranging from 30° C. to 60° C., and in particular ranging from 40° C. to 50° C. This melting point is a first-order temperature of change of state.

This melting point may be measured by any known method and in particular using a differential scanning calorimeter (DSC), for example the calorimeter sold under the name DSC Q2000 by the company TA Instruments.

Advantageously, the semi-crystalline polymer(s) to which the present disclosure applies has a number-average molecular mass of greater than or equal to 1000.

Advantageously, the semi-crystalline polymer(s) of the composition of the disclosure has a number-average molecular mass Mn ranging from 2000 to 800 000, preferably from 3000 to 500 000, better still from 4000 to 150 000 and especially less than 100 000 and better still from 4000 to 99 000. Preferably, they have a number-average molecular mass of greater than 5600, for example ranging from 5700 to 99 000.

For the purposes of the present disclosure, the expression "crystallizable chain or block" means a chain or block which, if it were obtained alone, would change from the amorphous state to the crystalline state reversibly, depending on whether the temperature is above or below the melting point. For the purposes of the present disclosure, a "chain" is a group of atoms, which are pendent or lateral relative to the polymer backbone. A "block" is a group of atoms belonging to the backbone, this group constituting one of the repeating units of the polymer. Advantageously, the "pendent crystallizable chain" may be a chain containing at least 6 carbon atoms.

Preferably, the crystallizable block(s) or chain(s) of the semi-crystalline polymers represent at least 30% of the total weight of each polymer and better still at least 40%. The semi-crystalline polymers of the present disclosure containing crystallizable blocks are block or multi-block polymers. They may be obtained via polymerization of a monomer containing reactive double bonds (or ethylenic bonds) or via polycondensation. When the polymers of the present disclosure are polymers containing crystallizable side chains, these side chains are advantageously in random or statistical form.

Preferably, the semi-crystalline polymers that may be used in the composition according to the present disclosure are of synthetic origin. Moreover, they do not comprise a polysaccharide backbone. In general, the crystallizable units (chains or blocks) of the semi-crystalline polymers according to the disclosure originate from monomer(s) containing crystallizable block(s) or chain(s), used for the manufacture of the semi-crystalline polymers.

According to the disclosure, the semi-crystalline polymer may be chosen from block copolymers comprising at least one crystallizable block and at least one amorphous block, and homopolymers and copolymers bearing at least one crystallizable side chain per repeating unit, and mixtures thereof.

The semi-crystalline polymers that may be used in the disclosure are in particular:
- block copolymers of polyolefins with controlled crystallization, especially those whose monomers are described in EP-A-0 951 897,
- polycondensates, especially of aliphatic or aromatic polyester type or of aliphatic/aromatic copolyester type,
- homopolymers or copolymers bearing at least one crystallizable side chain and homopolymers or copolymers bearing at least one crystallizable block in the backbone, for instance those described in document U.S. Pat. No. 5,156,911,
- homopolymers or copolymers bearing at least one crystallizable side chain, in particular containing fluoro group(s), as described in document WO-A-01/19333, and mixtures thereof.

In the last two cases, the crystallizable side chain(s) or block(s) are hydrophobic.

(i) Semi-Crystalline Polymers Containing Crystallizable Side Chains

Mention may be made in particular of those defined in documents U.S. Pat. No. 5,156,911 and WO-A-01/19333. They are homopolymers or copolymers comprising from 50% to 100% by weight of units resulting from the polymerization of one or more monomers bearing a crystallizable hydrophobic side chain.

These homopolymers or copolymers are of any nature, provided that they meet the conditions mentioned previously.

They can result:
- from the polymerization, especially the free-radical polymerization, of one or more monomers containing reactive double or ethylenic bond(s) with respect to a polymerization, namely a vinyl, (meth)acrylic or allylic group,
- from the polycondensation of one or more monomers bearing co-reactive groups (carboxylic acid, sulfonic acid, alcohol, amine or isocyanate), such as, for example, polyesters, polyurethanes, polyethers, polyureas or polyamides.

In general, these polymers are chosen especially from homopolymers and copolymers resulting from the polymerization of at least one monomer containing crystallizable chain(s) that may be represented by formula (I):

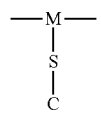

with M representing an atom of the polymer backbone, S representing a spacer and C representing a crystallizable group.

The crystallizable chains "—S—C" may be aliphatic or aromatic, and optionally fluorinated or perfluorinated. "S" especially represents the group (CH2)n or (CH2CH2O)n or (CH2O), which may be linear or branched or cyclic, with n being an integer ranging from 0 to 22. Preferably, "S" is a linear group. Preferably, "S" and "C" are different.

When the crystallizable chains "—S—C" are hydrocarbon-based aliphatic chains, they comprise hydrocarbon-based alkyl chains containing at least 11 carbon atoms and not more than 40 carbon atoms and better still not more than 24 carbon atoms. They are especially aliphatic chains or alkyl chains containing at least 12 carbon atoms, and they are preferably C14-C24 alkyl chains. When they are fluoroalkyl- or perfluoroalkyl-chains, they contain at least six fluorinated carbon atoms and especially at least 11 carbon atoms, at least six of which carbon atoms are fluorinated.

As examples of semi-crystalline polymers or copolymers bearing crystallizable chain(s), mention may be made of those resulting from the polymerization of one or more of the following monomers: (meth)acrylates of saturated alkyl with the alkyl group being C14-C24, perfluoroalkyl (meth)acrylates with a C11-C15 perfluoroalkyl group, N-alkyl (meth)acrylamides with the alkyl group being C14 to C24 with or without a fluorine atom, vinyl esters containing alkyl or perfluoro(alkyl) chains with the alkyl group being C14 to C24 (with at least 6 fluorine atoms per perfluoroalkyl chain), vinyl ethers containing alkyl or perfluoro(alkyl) chains with the alkyl group being C14 to C24 and at least 6 fluorine atoms per perfluoroalkyl chain, C14 to C24 alpha-olefins such as, for example, octadecene, para-alkylstyrenes with an alkyl group containing from 12 to 24 carbon atoms, and mixtures thereof.

When the polymers result from a polycondensation, the hydrocarbon-based and/or fluorinated crystallizable chains as defined above are borne by a monomer that may be a diacid, a diol, a diamine or a diisocyanate.

When the polymers that are the subject of the present disclosure are copolymers, they additionally contain from 0 to 50% of groups Y or Z resulting from the copolymerization:

α) of Y which is a polar or non-polar monomer or a mixture of the two:

When Y is a polar monomer, it is either a monomer bearing polyoxyalkylenated groups (especially oxyethylenated and/or oxypropylenated groups), a hydroxyalkyl (meth)acrylate, for instance hydroxyethyl acrylate, (meth)acrylamide, an N-alkyl(meth)acrylamide, an N,N-dialkyl(meth)acrylamide such as, for example, N,N-diisopropylacrylamide or N-vinylpyrrolidone (NVP), N-vinylcaprolactam, a monomer bearing at least one carboxylic acid group, for instance (meth)acrylic acid, crotonic acid, itaconic acid, maleic acid or fumaric acid, or bearing a carboxylic acid anhydride group, for instance maleic anhydride, and mixtures thereof.

When Y is a non-polar monomer, it may be an ester of the linear, branched or cyclic alkyl (meth)acrylate type, a vinyl ester, an alkyl vinyl ether, an α-olefin, styrene or styrene substituted with a C1 to C10 alkyl group, for instance α-methylstyrene.

For the purposes of the present disclosure, the term "alkyl" means a saturated group especially of C8 to C24, except where otherwise mentioned, and better still of C14 to C24.

β) of Z which is a polar monomer or a mixture of polar monomers. In this case, Z has the same definition as the "polar Y" defined above.

Preferably, the semi-crystalline polymers containing a crystallizable side chain are alkyl (meth)acrylate or alkyl (meth)acrylamide homopolymers with an alkyl group as defined above, and especially of C14-C24, copolymers of these monomers with a hydrophilic monomer preferably of different nature from (meth)acrylic acid, for instance N-vinylpyrrolidone or hydroxyethyl (meth)acrylate, and mixtures thereof.

(ii) Polymers Bearing in the Backbone at Least One Crystallizable Block

These polymers are especially block copolymers consisting of at least two blocks of different chemical nature, one of which is crystallizable.

The block polymers defined in patent U.S. Pat. No. 5,156,911 may be used;

Block copolymers of olefin or of cycloolefin containing a crystallizable chain, for instance those derived from the block polymerization of:

cyclobutene, cyclohexene, cyclooctene, norbornene (i.e. bicyclo(2,2,1)-2-heptene), 5-methylnorbornene, 5-ethylnorbornene, 5,6-dimethylnorbornene, 5,5,6-trimethylnorbornene, 5-ethylidenenorbornene, 5-phenylnorbornene, 5-benzylnorbornene, 5-vinylnorbornene, 1,4,5,8-dimethano-1,2,3,4,4a,5,8a-tetrahydronaphthalene, dicyclopentadiene, or mixtures thereof, with ethylene, propylene, 1-butene, 3-methyl-1-butene, 1-hexene, 4-methyl-1-pentene, 1-octene, 1-decene or 1-eicosene, or mixtures thereof.

and in particular copoly(ethylene/norbornene) blocks and (ethylene/propylene/ethylidene-norbornene) block terpolymers. Those resulting from the block copolymerization of at least two C2-C16, better still C2-C12 and even better still C4-C12-olefins such as those mentioned above and in particular block bipolymers of ethylene and of 1-octene may also be used.

The copolymers may be copolymers containing at least one crystallizable block, the copolymer residue being amorphous (at room temperature). These copolymers may also contain two crystallizable blocks of different chemical nature. The preferred copolymers are those that simultaneously contain at room temperature a crystallizable block and an amorphous block that are both hydrophobic and lipophilic, sequentially distributed; mention may be made, for example, of polymers containing one of the crystallizable blocks and one of the amorphous blocks below:

Block that is crystallizable by nature: a) of polyester type, for instance poly(alkylene terephthalate), b) of polyolefin type, for instance polyethylenes or polypropylenes.

Amorphous and lipophilic block, for instance amorphous polyolefins or copoly(olefin)s such as poly(isobutylene), hydrogenated polybutadiene or hydrogenated poly(isoprene).

As examples of such copolymers containing a crystallizable block and a separate amorphous block, mention may be made of:

α) poly(ε-caprolactone)-b-poly(butadiene) block copolymers, preferably used hydrogenated, such as those described in the article "Melting behaviour of poly(ε-caprolactone)-block-polybutadiene copolymers" from S. Nojima, Macromolecules, 32, 3727-3734 (1999), β) the hydrogenated block or multiblock poly(butylene terephthalate)-b-poly(isoprene) block copolymers cited in the article "Study of morphological and mechanical properties of PP/PBT" by B. Boutevin et al., Polymer Bulletin, 34, 117-123 (1995), γ) the poly(ethylene)-b-copoly(ethylene/propylene) block copolymers cited in the articles "Morphology of semicrystalline block copolymers of ethylene-(ethylene-alt-propylene)" by P. Rangarajan et al., Macromolecules, 26, 4640-4645 (1993) and "Polymer aggregates with crystalline cores: the system poly(ethylene)poly(ethylene-propylene)" by P. Richter et al., Macromolecules, 30, 1053-1068 (1997).

δ) the poly(ethylene)-b-poly(ethylethylene) block copolymers mentioned in the general article "Crystallization in block copolymers" by I. W. Hamley, Advances in Polymer Science, vol. 148, 113-137 (1999).

The semicrystalline polymers in the composition of the present disclosure may or may not be partially crosslinked, provided that the degree of crosslinking does not interfere with their dissolution or dispersion in the liquid fatty phase optionally present in the composition by heating above their melting point. It may then be a case of chemical crosslinking, by reaction with a multifunctional monomer during the polymerization. It may also be a case of physical crosslinking, which may then be due either to the establishment of bonds of hydrogen or dipolar type between groups borne by the polymer, for instance dipolar interactions between carboxylate ionomers, these interactions being in small amount and borne by the polymer backbone; or to a phase separation between the crystallizable blocks and the amorphous blocks, borne by the polymer.

Preferably, the semi-crystalline polymers of the composition according to the present disclosure are not crosslinked.

According to one particular embodiment of the disclosure, the polymer is chosen from copolymers resulting from the polymerization of at least one monomer containing a crystallizable chain chosen from saturated C14 to C24 alkyl (meth)acrylates, C11 to C15 perfluoroalkyl (meth)acrylates, C14 to C24 N-alkyl(meth)-acrylamides with or without a fluorine atom, vinyl esters containing C14 to C24 alkyl or perfluoroalkyl chains, vinyl ethers containing C14 to C24 alkyl or perfluoroalkyl chains, C14 to C24 alpha-olefins, para-alkylstyrenes with an alkyl group containing from 12 to 24 carbon atoms, with at least one optionally fluorinated C1 to C10 monocarboxylic acid ester or amide, which may be represented by the following formula (ω):

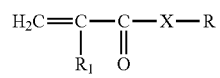

in which R1 is H or CH3, R represents an optionally fluorinated C1-C10 alkyl group and X represents O, NH or NR2 in which R2 represents an optionally fluorinated C1-C10 alkyl group.

According to one more particular embodiment of the present disclosure, the polymer is derived from a monomer containing a crystallizable chain chosen from saturated C14 to C22 alkyl (meth)acrylates and even more particularly poly(stearyl acrylate) or poly(behenyl acrylate).

As particular examples of structuring semi-crystalline polymers that may be used in the composition according to the present disclosure, mention may be made of polymers having the INCI name "Poly C10-C30 alkyl acrylate", for instance the Intelimer® products from the company Air Products, for instance the product Intelimer® IPA 13-1, which is a polystearyl acrylate and a melting point of 48° C. of a melting point, or the product Intelimer® IPA 13-6, which is a behenyl polymer.

The semi-crystalline polymers may especially be:

those described in Examples 3, 4, 5, 7, 9 and 13 of patent U.S. Pat. No. 5,156,911 containing a —COOH group, resulting from the copolymerization of acrylic acid and of C5 to C16 alkyl (meth)acrylate and more particularly of the copolymerization:

of acrylic acid, of hexadecyl acrylate and of isodecyl acrylate in a 1/16/3 weight ratio, of acrylic acid and of pentadecyl acrylate in a 1/19 weight ratio, of acrylic acid, of hexadecyl acrylate and of ethyl acrylate in a 2.5/76.5/20 weight ratio, of acrylic acid, of hexadecyl acrylate and of methyl acrylate in a 5/85/10 weight ratio, of acrylic acid and of octadecyl methacrylate in a 2.5/97.5 weight ratio, of hexadecyl acrylate, of polyethylene glycol methacrylate monomethyl ether containing 8 ethylene glycol units, and of acrylic acid in an 8.5/1/0.5 weight ratio.

It is also possible to use the structure "O" from National Starch, as described in document U.S. Pat. No. 5,736,125, with a melting point of 44° C., and also semi-crystalline polymers with crystallizable pendent chains comprising fluoro groups, as described in Examples 1, 4, 6, 7 and 8 of document WO-A-01/19333.

It is also possible to use the semi-crystalline polymers obtained by copolymerization of stearyl acrylate and of acrylic acid or NVP as described in document U.S. Pat. No. 5,519,063 or EP-A-550 745, with melting points of 40° C. and 38° C., respectively.

It is also possible to use the semi-crystalline polymers obtained by copolymerization of behenyl acrylate and of acrylic acid or NVP, as described in documents U.S. Pat. No. 5,519,063 and EP-A-550 745, with melting points of 60° C. and 58° C., respectively.

Preferably, the semi-crystalline polymers do not comprise any carboxylic groups.

Finally, the semi-crystalline polymers according to the present disclosure may also be chosen from waxy polymers obtained by metallocene catalysis, such as those described in patent application US 2007/0 031 361.

These polymers are homopolymers or copolymers of ethylene and/or propylene prepared via metallocene catalysis, i.e. by polymerization at low pressure and in the presence of a metallocene catalyst.

The weight-average molecular mass (Mw) of the waxes obtained via metallocene catalysis described in that document is less than or equal to 25 000 g/mol and ranges, for example, from 2000 to 22 000 g/mol and better still from 4000 to 20 000 g/mol.

The number-average molecular mass (Mn) of the waxes obtained via metallocene catalysis described in that document is preferably less than or equal to 15 000 g/mol and ranges, for example, from 1000 to 12 000 g/mol and better still from 2000 to 10 000 g/mol.

The polydispersity index I of the polymer is equal to the ratio of the weight-average molecular mass Mw to the number-average molecular mass Mn. Preferably, the polydispersity index of the waxy polymers is between 1.5 and 10, more preferably between 1.5 and 5, even more preferably between 1.5 and 3 and better still between 2 and 2.5.

The waxy homopolymers and copolymers may be obtained in a known manner from ethylene and/or propylene monomers, for example via metallocene catalysis according to the process described in document EP 571 882.

The homopolymers and copolymers of ethylene and/or propylene prepared via metallocene catalysis may be unmodified or "polar"-modified (polar-modified waxes, i.e. waxes modified such that they have the properties of a polar wax). The polar-modified waxy homopolymers and copolymers may be prepared in a known manner from unmodified waxy homopolymers and copolymers such as those described previously by oxidation with gases containing oxygen, such as air, or by grafting with polar monomers such as maleic acid or acrylic acid or alternatively derivatives of these acids. These two routes enabling polar modification of the polyolefins obtained via metallocene catalysis are described, respectively, in documents EP 890 583 and U.S. Pat. No. 5,998,547, for example, the content of these two documents being incorporated herein by reference.

According to the present disclosure, the polar-modified homopolymers and copolymers of ethylene and/or propylene prepared via metallocene catalysis that are particularly preferred are polymers modified such that they have hydrophilic properties. Examples that may be mentioned include ethylene and/or propylene homopolymers or copolymers modified by the presence of hydrophilic groups such as maleic anhydride, acrylate, methacrylate, polyvinylpyrrolidone (PVP), etc.

Waxy ethylene and/or propylene homopolymers or copolymers modified by the presence of hydrophilic groups such as maleic anhydride or acrylate are particularly preferred. Examples that may be mentioned include:

polypropylene waxes modified with maleic anhydride (PPMA) sold by the company Clariant, or polypropylene-ethylene-maleic anhydride copolymers, such as those sold by the company Clariant under the name LicoCare, for instance LicoCare PP207 LP3349, LicoCare CM401 LP3345, LicoCare CA301 LP3346 and LicoCare CA302 LP3347 or alternatively the unmodified polyethylene waxes sold by the company Clariant, such as the product LicoCare PE 102 LP3329.

(II) Semi-Crystalline or Crystalline Wax

Semi-crystalline or crystalline waxes are chosen from polar and apolar hydrocarbon-based waxes, or mixtures thereof.

The term "wax(es)", under consideration in the context of the present disclosure are generally lipophilic compounds that are solid at room temperature (25° C.), with a solid/liquid reversible change of state, having a melting point of greater than or equal to 30° C., which may be up to 200° C. and especially up to 120° C.

In particular, the semi-crystalline or crystalline waxes that are suitable for the present disclosure may have a melting point of greater than or equal to 40° C., and less than or equal to 60° C. Furthermore, the semi-crystalline or crystalline waxes that are suitable for the present disclosure may have a melting point of less than or equal to 100° C., preferably less than or equal to 85° C., and especially less than or equal to 70° C.

The semi-crystalline or crystalline waxes used in the present disclosure can be semi-crystalline or crystalline apolar or polar wax.

(i) Apolar Wax

For the purposes of the present disclosure, the term "apolar wax" means a wax whose solubility parameter at 25° C. as defined below, $\delta a$, is equal to 0 $(J/cm3)^{1/2}$.

Apolar waxes are in particular hydrocarbon-based waxes constituted solely of carbon and hydrogen atoms, and free of heteroatoms such as N, O, Si and P.

The term "hydrocarbon-based wax" means a wax formed essentially from, or even constituted of, carbon and hydrogen atoms, and optionally oxygen and nitrogen atoms, and not containing any silicon or fluorine atoms. It may contain alcohol, ester, ether, carboxylic acid, amine and/or amide groups.

The definition and calculation of the solubility parameters in the Hansen three-dimensional solubility space are described in the article by C. M. Hansen: The three-dimensional solubility parameters, J. Paint Technol. 39, 105 (1967).

According to this Hansen space:

δD characterizes the London dispersion forces derived from the formation of dipoles induced during molecular impacts;

δp characterizes the Debye interaction forces between permanent dipoles and also the Keesom interaction forces between induced dipoles and permanent dipoles;

δh characterizes the specific interaction forces (such as hydrogen bonding, acid/base, donor/acceptor, etc.); and δa is determined by the equation: $\delta a = (\delta p^2 + \delta h^2)^{1/2}$ The parameters δp, δh, δD and δa are expressed in $(J/cm3)^{1/2}$.

More particularly, the apolar wax may be chosen from microcrystalline waxes, paraffin waxes, ozokerite, polyethylene waxes, polymethylene waxes and microwaxes, and mixtures thereof.

As microcrystalline waxes that may be used, mention may be made of Multiwax W 445® sold by the company Sonneborn, and Microwax HW® and Base Wax 30540® sold by the company Paramelt.

An ozokerite that may be mentioned is Ozokerite Wax SP 1020 P.

Polyethylene waxes that may be mentioned include Performalene 500-L Polyethylene and Performalene 400 Polyethylene sold by New Phase Technologies.

Polymethylene waxes that may be mentioned include the Polymethylene Wax sold under the reference Cirebelle 303, which has a melting point of 61° C. to 67° C.; and the Polymethylene Wax sold under the reference Cirebelle 108, which has a melting point of 79° C. to 84° C., sold by Cirebelle.

As microwaxes that may be used in the compositions according to the present disclosure as apolar wax, mention may be made especially of polyethylene microwaxes such as those sold under the names Micropoly 200®, 220®, 220L® and 250S® by the company Micro Powders.

(ii) Polar Wax

For the purposes of the present disclosure, the term "polar wax" means a wax whose solubility parameter at 25° C., δa, is other than 0 $(J/cm3)^{1/2}$.

The term "polar wax" here means a wax whose chemical structure is formed essentially from, or even constituted of, carbon and hydrogen atoms, and comprising at least one highly electronegative heteroatom such as an oxygen, nitrogen, silicon or phosphorus atom.

As the hydrocarbon-based polar wax, a wax chosen from ester waxes is in particular preferred.

The term "hydrocarbon-based" means a compound formed essentially from, or even constituted of, carbon and hydrogen atoms, and optionally oxygen and nitrogen atoms, and not containing any silicon or fluorine atoms.

According to the present disclosure, the term "ester wax" means a wax comprising at least one ester function.

The following may especially be used as the ester wax: ester waxes such as those chosen from:

i) waxes of formula R1COOR2 in which R1 and R2 represent linear, branched or cyclic aliphatic chains in which the number of atoms ranges from 10 to 50, which may contain a heteroatom such as O, N or P and whose melting point ranges from 25 to 120° C.

In particular, use may be made, as the ester wax, of a C20-C40 alkyl (hydroxystearyloxy)stearate (the alkyl group comprising from 20 to 40 carbon atoms), alone or as a mixture, or a C20-C40 alkyl stearate. Such waxes are especially sold under the names Kester Wax K 82 P®, Hydroxypolyester K 82 P®, Kester Wax K 80 P® and Kester Wax K82H by the company Koster Keunen.

ii) glycol and butylene glycol montanate (octacosanoate) waxes such as the wax Licowax KPS Flakes (INCI name: glycol montanate) sold by the company Clariant.

iii) bis(1,1,1-trimethylolpropane) tetrastearate, sold under the name Hest 2T-4S® by the company Heterene.

iv) diester waxes of a dicarboxylic acid of general formula R3-(—OCO—R4-COO—R5), in which R3 and R5 are identical or different, preferably identical and represent a C4-C30 alkyl group (alkyl group comprising from 4 to 30 carbon atoms) and R4 represents a linear or branched C4-C30 aliphatic group (alkyl group comprising from 4 to 30 carbon atoms) which may or may not contain one or more unsaturated groups, and preferably that is linear and unsaturated.

v) Mention may also be made of the waxes obtained by catalytic hydrogenation of animal or plant oils having linear or branched C8-C32 fatty chains, for example such as hydrogenated jojoba oil, hydrogenated sunflower oil, hydrogenated castor oil, hydrogenated coconut oil, and also the waxes obtained by hydrogenation of castor oil esterified with cetyl alcohol, such as those sold under the names Phytowax Ricin 16L64® and 22L73® by the company Sophim. Such waxes are described in patent application FR-A-2792190 and the waxes obtained by hydrogenation of olive oil esterified with stearyl alcohol such as that sold under the name Phytowax Olive 18 L 57, or the like.

v) beeswax, synthetic beeswax, polyglycerolated beeswax, carnauba wax, candelilla wax, oxypropylenated lanolin wax, rice bran wax, ouricury wax, esparto grass wax, cork fibre wax, sugar cane wax, Japan wax, sumach wax, montan wax, orange wax, laurel wax and hydrogenated jojoba wax. Candelilla wax is preferably used.

The oil-in-water compositions described herein may include one or more thickeners. The thickeners may be in an amount from 0.1, 0.2, 0.3, 0.4, 0.5, 0.6, 0.7, 0.8, 0.9, 1.0, 1.2, 1.4, 1.6, 1.8, 2.0, 2.2, 2.4, 2.5 to about 2.5, 2.6, 2.8, 3.0, 3.2, 3.4, 3.6, 3.8, 4.0, 4.2, 4.4, 4.6, 4.8 or 5 wt. % based on the total weight of the oil-in-water composition.

Film Formers

Film-formers may be incorporated into the sunscreen to ensure even coverage and improved water resistance.

The one or more film formers may be selected from silicone acrylates. In some particular embodiments the one or more film former comprises a silicone acrylate copolymer. Some representative examples of silicone acrylates film formers include dimethicone (and) dimethiconol, dimethicone (and) acrylates/dimethicone copolymer, and acrylates/ polytrimethylsiloxymethacrylate copolymer.

In some representative embodiments, a film former is selected from one or a combination of dimethicone (and) dimethiconol, and dimethicone (and) acrylates/dimethicone copolymer.

As silicone acrylates used in the composition of the instant disclosure, mention may be made in particular of the silicon acrylates (INCI name: acrylates/dimethicone copolymer) sold by the company Shin-Etsu under the tradenames KP-561 in which the polymer is not dispersed in solvent, KP-541 in which the copolymer is dispersed in isopropyl alcohol, KP-545 in which the copolymer is dispersed in cyclopentasiloxane, and KP-550 in which the copolymer is dispersed in isododecane.

A particularly preferred silicone acrylate is a graft copolymer having an acrylic acid polymer backbone and polydimethylsiloxane side chains, commercially available from Shin Etsu under the tradenames KSP545 and KSP545L.

The oil-in-water compositions described herein may include one or more thickeners. The total amount of thickeners may be in an amount from 0.1, 0.2, 0.3, 0.4, 0.5, 0.6, 0.7, 0.8, 0.9, 1.0, 1.2, 1.4, 1.6, 1.8, 2.0, 2.2, 2.4, 2.5 to about 2.5, 2.6, 2.8, 3.0, 3.2, 3.4, 3.6, 3.8, 4.0, 4.2, 4.4, 4.6, 4.8 or 5 wt. % based on the total weight of the oil-in-water composition.

Emulsifiers

The appropriate emulsifier(s) often depends on the UV filter(s) and other components included in the sunscreen composition. Emulsifiers include nonionic, cationic, anionic, and amphoteric or zwitterionic emulsifiers. In some cases, however, the emulsifier is a nonionic emulsifier such as, for example, a polyol ester, a glycerol ether, an oxyethylenated and/or oxypropylenated ether, and/or an ethylene glycol polymer, and mixture thereof. Often, the sunscreen compositions are in the form of an emulsion.

In one embodiment, the nonionic emulsifier is a polyol ester and/or an ethylene glycol polymer. In one embodiments, the nonionic emulsifier is a combination of glyceryl stearate and PEG-100 stearate. In some embodiments, the one or more emulsifiers is present from about 0.1 to about 10 wt. % based on the total weight of the oil-in-water composition.

Emulsifiers are well known in the art and include amphoteric, anionic, cationic or nonionic emulsifiers, used alone or as a mixture, and optionally with a co-emulsifier.

The emulsifiers are chosen in an appropriate manner according to the emulsion to be obtained.

For O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

The type and amount of emulsifier will vary depending on the type of UV filter(s) and other components included in the sunscreen composition.

In some cases, the total amount of emulsifier may be from about 0.1, 0.2, 0.3, 0.4, 0.5, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0 to about 5.0, 5.2, 5.4, 5.6, 5.8, 6.0, 6.2, 6.4, 6.6, 6.8, 7.0, 7.3, 7.4, 7.6, 7.8, 8.0, 8.2, 8.4, 8.6, 8.8, 9.0, 9.2, 9.4, 9.6, 9.8 or 10 wt. % based on the total weight of the oil-in-water composition.

The sunscreen composition is often in the form of an emulsion.

The sunscreen compositions of the instant disclosure are useful in methods for protecting skin from sun damage; such methods comprise applying an effective amount of the oil-in-water composition to the skin or hair.

The instant disclosure relates to method for boosting SPF of a sunscreen composition comprising UV filters, the method comprising adding antioxidants and SPF booster within a certain range to the sunscreen composition, thereby boosting the SPF of the UV filters.

More exhaustive but non-limiting lists of components useful in the compositions disclosed herein are provided later, after the below description of the sunscreen compositions UV Filters UV filters are well known in the art for their use in stopping UV radiation. For example, the UV filter may be one or more organic UV filters and/or one or more inorganic UV filters. Non-limiting examples of UV filters include:

i. Sparingly soluble UV filters (not appreciably soluble in either water or oil) such as Methylene Bis-Benzotriazolyl Tetramethylbutylphenol, Tris-Biphenyl Triazine, Methanone, 1,1'-(1,4-piperazinediyl)bis[1-[2-[4-(diethylamino)-2-hydroxybenzoyl]phen-yl]- and mixtures thereof.

ii. Oil soluble organic UV filters (at least partially soluble in oil or organic solvent), such as Bis-Ethylhexyloxyphenol Methoxyphenyl Triazine, Butyl Methoxydibenzoylmethane (BMBM), Oxybenzone, Sulisobenzone, Diethylhexyl Butamido Triazone (DBT), Drometrizole Trisiloxane, Ethylhexyl Methoxycinnamate (EHMC), Ethylhexyl Salicylate (EHS), Ethylhexyl Triazone (EHT), Homosalate, Isoamyl p-Methoxycinnamate, 4-Methylbenzylidene Camphor, Octocrylene (OCR), Polysilicone-15, and Diethylamino Hydroxy Benzoyl Hexyl Benzoate (DHHB);

iii. Inorganic UV filters such as titanium oxide and zinc oxide, iron oxide, zirconium oxide and cerium oxide; and iv. Water soluble UV filters such as Phenylbenzimidazole Sulfonic Acid (PBSA), Sulisobenzone-sodium salt, Benzydilene Camphor Sulfonic Acid, Camphor Benzalkonium Methosulfate, Cinoxate, Disodium Phenyl Dibenzylimidazole Tetrasulfonate, Terephthalylidene Dicamphor Sulfonic Acid, PABA, and PEG-25 PABA.

In some instances, the UV filter is one or more of: a para-aminobenzoic acid derivative, a salicylic derivative, a cinnamic derivative, a benzophenone or an aminobenzophenone, an anthranillic derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, a chalcone, or a mixture thereof.

Furthermore, combinations of UV filters may be used. For example, the combination of UV filters may be octocrylene, avobenzone (butyl methoxydibenzoylmethane), oxybenzone (benzophenone-3), octisalate (ethylhexyl salicylate), and homosalate, as described in application Ser. No. 13/304, 195, which is incorporated herein by reference in its entirety. For instance, this combination of UV filters may be used in the following ratios relative to avobenzone:

the ratio of octocrylene to avobenzone is 1.6:1.0 to 2.4:1.0;

the ratio of oxybenzone to avobenzone 1.0:1.0 to 1.6:1.0;

the ratio of octisalate to avobenzone is 0.8:1.0 to 1.3:1.0; and the ratio of homosalate to avobenzone is 2.8:1.0 to 4.3:1.

Furthermore, the ratio of each UV filter relative to avobenzone may be about: 2.0:1.0:1.3:1.1:3.6 (octocrylene: avobenzone:oxybenzone:octisalate:homosalate).

In another embodiment, the at least one UV filter is a combination of UV filters comprising octocrylene, avobenzone, octisalate, and homosalate, and optionally oxybenzone, as described in application Ser. No. 13/304,202, which is incorporated herein by reference in its entirety. For instance, this combination of UV filters may be used in the following ratios relative to avobenzone:

the ratio of octocrylene to avobenzone is 1.6:1.0 to 2.4:1.0, the ratio of oxybenzone to avobenzone 0.0:1.0 to 0.016:1.0, the ratio of octisalate to avobenzone is 1.3:1.0 to 2.0:1.0, and the ratio of homosalate to avobenzone is 2.3:1.0 to 3.6:1.

Furthermore, the ratio of each UV filter relative to avobenzone may be about: 2.0:1.0:0.0:1.7:3.0 (octocrylene: avobenzone:oxybenzone:octisalate:homosalate).

In another embodiment, the at least one UV filter is a combination of UV filters comprising octocrylene, butyl methoxydibenzoylmethane, bis-ethylhexyloxyphenol methoxyphenyl triazine, ethylhexyl triazone, terephthalylidene dicamphor sulfonic acid, and drometrizole trisiloxane, as described in application Ser. No. 13/719,328, which is incorporated herein by reference in its entirety. For instance, this combination of UV filters may be used in the following ratios relative to butyl methoxydibenzoylmethane:

the ratio of octocrylene to butyl methoxydibenzoylmethane is 0.8:1.0 to 1.5:1.0;

the ratio of bis-ethylhexyloxyphenol methoxyphenyl triazine to butyl methoxydibenzoylmethane 0.3:1.0 to 0.8:1.0;

the ratio of ethylhexyl triazone to butyl methoxydibenzoylmethane is 0.3:1.0 to 1.0:1.0;

the ratio of terephthalylidene dicamphor sulfonic acid to butyl methoxydibenzoylmethane is 0.1:1.0 to 0.5:1.0; and the ratio of drometrizole trisiloxane to butyl methoxydibenzoylmethane is 0.3:1.0 to 1.0:1.0.

Furthermore, the ratio of each UV filter relative to butyl methoxydibenzoyl-methane may be about: 1.2:1.0:0.5:0.6: 0.4:0.6 (octocrylene:butyl methoxy-dibenzoylmethane:bis-ethylhexyloxyphenol methoxyphenyl triazine:ethylhexyl triazone:terephthalylidene dicamphor sulfonic acid: drometrizole trisiloxane).

In another embodiment, the at least one UV filter is a combination of UV filters comprising octocrylene, butyl methoxydibenzoylmethane, ethylhexyl triazone, terephthalylidene dicamphor sulfonic acid, and drometrizole trisiloxane, as described in application Ser. No. 13/719,351, which is incorporated herein by reference in its entirety. For instance, this combination of UV filters may be used in the following ratios relative to butyl methoxydibenzoylmethane:

the ratio of octocrylene to butyl methoxydibenzoylmethane is 0.6:1.0 to 1.25:1.0;

the ratio of ethylhexyl triazone to butyl methoxydibenzoylmethane is 0.4:1.0 to 1.0:1.0;

the ratio of terephthalylidene dicamphor sulfonic acid to butyl methoxydibenzoylmethane is 0.3:1.0 to 0.7:1.0; and the ratio of drometrizole trisiloxane to butyl methoxydibenzoylmethane is 0.4:1.0 to 1.1:1.0.

Furthermore, the ratio of each UV filter relative to butyl methoxydibenzoyl-methane may be about: 1.0:1.0:0.7:0.5: 0.7 (octocrylene:butyl methoxydibenzoylmethane:ethylhexyl triazone:terephthalylidene dicamphor sulfonic acid: drometrizole trisiloxane).

In another embodiment, the at least one UV filter is a combination of UV filters comprising octocrylene, butyl methoxydibenzoylmethane, bis-ethylhexyloxyphenol methoxyphenyl triazine, terephthalylidene dicamphor sulfonic acid, and drometrizole trisiloxane, as described in application Ser. No. 13/719,368, which is incorporated herein by reference in its entirety. For instance, this combination of UV filters may be used in the following ratios relative to butyl methoxydibenzoylmethane:

the ratio of octocrylene to butyl methoxydibenzoylmethane is 0.8:1.0 to 1.2:1.0;

the ratio of bis-ethylhexyloxyphenol methoxyphenyl triazine to butyl methoxydibenzoylmethane is 0.2:1.0 to 0.6:1.0;

the ratio of terephthalylidene dicamphor sulfonic acid to butyl methoxydibenzoylmethane is 0.0.25:1.0 to 0.75: 1.0; and the ratio of drometrizole trisiloxane to butyl methoxydibenzoylmethane is 0.4:1.0 to 0.8:1.0.

Furthermore, the ratio of each UV filter relative to butyl methoxydibenzoyl-methane may be about: 1.0:1.0:0.4:0.4: 0.6 (octocrylene:butyl methoxydibenzoylmethane:bis-ethylhexyloxyphenol methoxyphenyl triazine:terephthalylidene dicamphor sulfonic acid:drometrizole trisiloxane).

In another embodiment, the at least one UV filter is a combination of UV filters comprising octocrylene, butyl methoxydibenzoylmethane, bis-ethylhexyloxyphenol methoxyphenyl triazine, terephthalylidene dicamphor sulfonic acid, and drometrizole trisiloxane, as described in application Ser. No. 13/719,374, which is incorporated herein by reference in its entirety. For instance, this combination of UV filters may be used in the following ratios relative to butyl methoxydibenzoylmethane is as follows:

the ratio of octocrylene to butyl methoxydibenzoylmethane is 0.8:1.0 to 1.3:1.0;

the ratio of bis-ethylhexyloxyphenol methoxyphenyl triazine to butyl methoxydibenzoylmethane is 0.1:1.0 to 0.6:1.0;

the ratio of ethylhexyl triazone to butyl methoxydibenzoylmethane is 0.2:1.0 to 0.6:1.0; and the ratio of drometrizole trisiloxane to butyl methoxydibenzoylmethane is 0.3:1.0 to 0.7:1.0.

Furthermore, the ratio of each UV filter relative to butyl methoxydibenzoyl-methane may be about: 1.0:1.0:0.3:0.5: 0.5 (octocrylene:butyl methoxydibenzoylmethane:bis-ethylhexyloxyphenol methoxyphenyl triazine:ethylhexyl triazone:drometrizole trisiloxane).

In another embodiment, the at least one UV filter is a combination of UV filters comprising octocrylene, butyl methoxydibenzoylmethane, bis-ethylhexyloxyphenol methoxyphenyl triazine, terephthalylidene dicamphor sulfonic acid, and terephthalylidene dicampohor sulfonic acid, as described in application Ser. No. 13/719,393, which is incorporated herein by reference in its entirety. For instance, this combination of UV filters may be used in the following ratios relative to butyl methoxydibenzoylmethane is as follows:

the ratio of octocrylene to butyl methoxydibenzoylmethane is 0.8:1.0 to 1.6:1.0;

the ratio of bis-ethylhexyloxyphenol methoxyphenyl triazine to butyl methoxydibenzoylmethane is 0.2:1.0 to 0.6:1.0;

the ratio of ethylhexyl triazone to butyl methoxydibenzoylmethane is 0.3:1.0 to 0.6:1.0; and the ratio of terephthalylidene dicampohor sulfonic acid to butyl methoxydibenzoylmethane is 0.01:1.0 to 0.3:1.0.

Furthermore, the ratio of each UV filter relative to butyl methoxydibenzoyl-methane may be about: 1.2:1.0:0.3:0.5: 0.1 (octocrylene:butyl methoxydibenzoylmethane:bis-ethylhexyloxyphenol methoxyphenyl triazine:ethylhexyl triazone:terephthalylidene dicampohor sulfonic acid).

Active Agents

Sunscreen compositions according to the present disclosure can optionally further include active agents. Suitable active agents include, for example, anti-acne agents, antimicrobial agents, anti-inflammatory agents, analgesics, anti-erythemal agents, antiruritic agents, antiedermal agents, antipsoriatic agents, antifungal agents, skin protectants, vitamins, antioxidants, scavengers, antiirritants, antibacterial agents, antiviral agents, antiaging agents, protoprotection agents, hair growth enhancers, hair growth inhibitors, hair removal agents, antidandruff agents, anti-seborrheic agents, exfoliating agents, wound healing agents, anti-ectoparacitic agents, sebum modulators, immunomodulators, hormones, botanicals, moisturizers, astringents, cleansers, sensates, antibiotics, anesthetics, steroids, tissue healing substances, tissue regenerating substances, hydroxyalkyl urea, amino acids, peptides, minerals, ceram ides, biohyaluronic acids, vitamins, skin lightening agents, self-tanning agents, coenzyme Q10, niacinimide, capcasin, caffeine, and any combination of any of the foregoing.

Adjuvants

Sunscreen compositions according to the present disclosure can optionally include one or more adjuvants, such as pH adjusters, emollients, humectants, conditioning agents, moisturizers, chelating agents, propellants, rheology modifiers and emulsifiers such as gelling agents, colorants, fragrances, odor masking agents, UV stabilizer, preservatives, and any combination of any of the foregoing. Examples of pH adjusters include, but are not limited to, aminomethyl propanol, aminomethylpropane diol, triethanolamine, triethylamine, citric acid, sodium hydroxide, acetic acid, potassium hydroxide, lactic acid, and any combination thereof.

Suitable conditioning agents include, but are not limited to, cyclomethicone; petrolatum; dimethicone; dimethiconol; silicone, such as cyclopentasiloxane and diisostearoyl trimethylolpropane siloxy silicate; sodium hyaluronate; isopropyl palmitate; soybean oil; linoleic acid; PPG-12/saturated methylene diphenyldiisocyanate copolymer; urea; amodimethicone; trideceth-12; cekimonium chloride; diphenyl dimethicone; propylene glycol; glycerin; hydroxyalkyl urea; tocopherol; quaternary amines; and any combination thereof.

Suitable preservatives include, but are not limited to, chlorophenesin, sorbic acid, disodium ethylenedinitrilotetraacetate, phenoxyethanol, methylparaben, ethylparaben, propylparaben, phytic acid, imidazolidinyl urea, sodium dehydroacetate, benzyl alcohol, methylehloroisothiazolinone, methylisothiazolinone, and any combination thereof. The sunscreen composition generally contains from about 0.001% to about 20% by weight of preservatives, based on 100% weight of total sunscreen composition and heat-protective composition. In another aspect, the composition contains from about 0.1% to about 10%.

The above lists are only examples and not limiting.

Implementation of the present disclosure is provided by way of the following examples. The examples serve to illustrate the technology without being limiting in nature.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular.

The expression "at least one" means one or more and thus includes individual components as well as mixtures/combinations.

All ranges and values disclosed herein are inclusive and combinable. For examples, any value or point described herein that falls within a range described herein can serve as a minimum or maximum value to derive a sub-range, etc.

All numbers, amounts, ranges, etc., are intended to be modified by the term "about," whether or not so expressly stated. Similarly, a range given of "about 1% to 10%" is intended to have the term "about" modifying both the 1% and the 10% endpoints.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

While the disclosure has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

Example 1

Inventive Composition

The following Examples are provided for illustrative purposes only, and are not intended to be limiting.

TABLE 1

| | Inventive Example | | | |
|---|---|---|---|---|
| Claim component | | INCI US | Example A (Wt. %) | Phase |
| a | Antioxidants | Diethylhexyl Syringylidenemalonate | 0.9 | B |
| | | Tocopherol | 0.5 | |
| b | SPF Booster | Styrene/Acrylates Copolymer | 1.73 | A1 |

TABLE 1-continued

| Claim component | | INCI US | Example A (Wt. %) | Phase |
|---|---|---|---|---|
| | | Inventive Example | | |
| c | Acrylates Crosspolymers | Acrylates/C10-30 Alkyl Acrylate Crosspolymer | 0.3 | A1 |
| d | Organic UV Filters | Octocrylene | 10 | B |
| | | Homosalate | 15 | B |
| | | Ethylhexyl Salicylate | 5 | B |
| | | Butyl Methoxydibenzoylmethane (avobenzone) | 3 | B |
| | Total UV Filters | | 33 | |
| e | Thickener | Poly C10-30 Alkyl Acrylate | 2 | B |
| f | Film Former | Acrylates/Dimethicone Copolymer | 0.9 | B |
| g | Emulsifiers | Glyceryl Stearate | 0.75 | B |
| | | Peg-100 Stearate | 0.75 | B |
| | | Potassium Cetyl Phosphate | 0.5 | |
| | Silicone compound | Dimethicone | 3.9 | B |
| | Water soluble solvent | Glycerin | 3.6 | A1 |
| | Misc. | Salts, Preservatives, Ph Adjusters, Skin actives, Gum, Vitamin, Etc. | 3.5 | |
| | Water | | >42.6 | |

In making the formulations in the above table, the following procedure was used.
1. The deionized water and glycerin were added into a beaker.
2. Using the Silverson, styrene/acrylates copolymer were added and mixed for 10-15 min.
3. While these raw materials were mixing, the oil phase was weighed out (B).
4. After the mixture in the beaker under the Silverson was homogeneous, the mixture was added to the main kettle.
5. The main kettle was heated to 75 C and water phase ingredients were added. Water phase thickeners were added slowly with scraping down.
6. Once water phase was homogeneous and oil phase was mixed and uniform, oil phase was added into the main kettle slowly. Mixed in 5 min intervals while checking emulsion.
7. Maintained the temperature at 75 C and performed a microscope check.
8. Film formers were add. Mixed 2-3 min for each raw materials.
9. Once homogenous, the cool down to 25 C began.
10. Between 45-55 C, pH adjuster was added and mixed for 5 min.
11. Below 30 C skin active ingredients were add and mixed with sweeps only for 5 min.
12. The mixture was cooled to 25 C.

The composition was shown to have very high SPF as well as a water resistance. The results are shown in the next section.

Example 2

Properties Evaluation

The compositions in the table below were prepared as described above and the SPF, sensorial properties and stability were measured. The results were reported in Table 2 below.

TABLE 2

| | Comp. Ex. A | Comp. Ex. B | Example A |
|---|---|---|---|
| | Properties | | |
| Filters + Boosters | | | |
| Architecture | W/O | O/W, Lotion | O/W, Lotion |
| Avobenzone | 3 | 3 | 3 |
| Homosalate | 15 | 15 | 15 |
| Octisalate | 5 | 5 | 5 |
| Octocrylene | 10 | 10 | 10 |
| Diethylhexyl syringylidenmalonate | 1 | 1 | 1 |
| Styrene/Acrylates copolymer (SPF boosters) | 2.01 | 7.8 | 2.01 |
| Tocopherol | 0.5 | 0.5 | 0.5 |

TABLE 2-continued

| | Properties | | |
|---|---|---|---|
| | Comp. Ex. A | Comp. Ex. B | Example A |
| Results | | | |
| in-vitro SPF | 113.94 | 79.03 | 174.67 |
| sensorial | very light fluid, slight greasiness, soft, dry finish | slight greasiness, cooling sensation, dry finish | non greasy, hydrating, soft, velvety finish |
| stability (2 weeks × 60 C.) | Change in color: yellowing Separation | Slightly textured Slight pulling/separation on top surface area | OK |

In Table 2, an Inventive Example A of the composition is shown in comparison to two non-inventive examples, Comparative Example A and Comparative Example B. The architecture of the Inventive Example A is an oil-in-water composition comprising an organic UV sun filter system, Diethylhexyl syringylidenemalonate at 1 wt. %, Styrene/Acrylates copolymer (SPF boosters) at 2.01 wt. % and Tocopherol at 0.5 wt. %. The architecture of the Comparative Example A is a water-in-oil composition comprising an organic UV sun filter system, Diethylhexyl syringyliden-emalonate at 1 wt %, Styrene/Acrylates copolymer (SPF boosters) at 2.01 wt. % and Tocopherol at 0.5 wt. %. The architecture of the Comparative Example B is an oil-in-water composition comprising an organic UV sun filter system, Diethylhexyl syringylidenemalonate at 1 wt %, Styrene/Acrylates copolymer (SPF boosters) at 7.8 wt % and Tocopherol at 0.5 wt. %.

The SPF for the three compositions, as well as their sensorial properties and their stabilities were measured and compared. It was observed that Inventive Example A exhibited superior properties compare to Comparative Examples A and B in terms of SPF, sensorial effects and stability.

SPF Results

The SPF were measured in vitro using a Labsphere 2000S UV analyzer. Each formulation (1.2 mg sample per cm$^2$ substrate) was weighed out on the rough surface of a PMMA plate. The formulations were then evenly spread using a circular motion following by a horizontal spreading movement onto the plate. Then, the plates were left to dry for 15 minutes. After drying, the treated plates were analyzed using Labsphere. Each treated plate was subjected to 5 measurements.

The SPF value measured for the three compositions were very different. The Inventive Example A exhibited an unexpected and surprisingly SPF value of SPF 174.67. Comparative Example A and B, respectively, exhibited SPF values of 113.94 and 79.03. The results were unexpected since Inventive Example A and Comparative Example A comprised the same amount of organic UV sun filter system, diehtylhexyl syringilidenemalonate and Tocopherol. Thus, it showed that the combination of SPF boosters and antioxidants in an oil-in-water architecture surprisingly increased the SPF value of the composition of 53%. It is not enough to increase only the amount of SPF booster in order to increase the SPF value. Likewise, the SPF values between Inventive Example A and Comparative Example B were also unexpected since Inventive Example A and Comparative Example B had both an oil-in-water architecture with an organic UV sun filter system, diethylhexyl syringilidenemalonate and Tocopherol, and increasing the amount of styrene/acrylates copolymer (SPF Booster) from 2.01% to 7.8% did not increase the SPF value of Comparative Example B. Therefore, the specific combination in Inventive Example A of UV sun filter system with diethylhexyl syringilidenemalonate and Tocopherol in a certain amount demonstrated the unexpected and surprising results on the increase of the SPF value.

Sensorial Properties

The sensorial properties were very different for the three compositions. The Inventive Example A exhibited very nice sensorial properties. The composition was not greasy, showed some hydrating properties and a soft and velvety finish that was not observed in Comparative Example A and B.

Stability (2 weeks at 60 C)

The Inventive Example A was very stable after being exposed at a temperature of 60 degree C. for two weeks. Comparative Example A exhibited a change in color and some separation. Comparative Example B was not smooth and showed some pulling/separation on the top surface area.

Example 3

Water Resistance Duration: 80 Minutes

The Water Resistance properties and the SPF were measured in vivo. The in vivo method were the FDA approved method. The results were reported in Table 3 below.

TABLE 3

| | SPF* StaticValue | SPF WR*Value |
|---|---|---|
| Inventive Formula A | | |
| Number of Subjects (N) | 10 | 10 |
| Mean of SPF Value | 118.80 | 112.6, WR 80 mins |
| Comparative Example B | | |
| Number of Subjects (N) | 10 | 10 |
| Mean of SPF Value | 72.18 | 61.15, WR 40 mins |

SPF* = Sun Protection Factor
SPF Static** Value = refers to the SPF determined without water immersion
WR*** = Water Resistance The SPF of the Inventive Formula A was tested on 10 subjects yielded the mean SPF 118.80.

The SPF of the Inventive Formula when tested on 10 subjects under 80 minutes water resistant conditions yielded the mean SPF 112.6.

The SPF of the Comparative Example B was tested on 10 subjects yielded the mean SPF 72.18.

The SPF of the Comparative Example B when tested on 10 subjects under 40 minutes water resistant conditions yielded the mean SPF under SPF 61.15.

According to the data from Table 3, the Inventive Formula A exhibited a very good water resistance, even after 80 minutes of immersion. Indeed, the SPF Static Value was measured at 118.80. After 80 minutes of immersion, the SPF WR Value was measured to be 112.6.

According to the data from Table 3, the Comparative Example B didn't exhibit a good water resistance compare to the Inventive Formula A. Indeed, after 80 minutes of immersion, the SPF value was measured to be 61.15.

The results showed unexpected results regarding the water resistance of the Inventive Formula after immersion of 80 minutes.

The invention claimed is:

1. An oil-in-water composition comprising:
   a) from about 0.1 to about 5 wt. % of one or more antioxidants selected from diethylhexyl syringylidene malonate, tocopherol and mixture thereof,
   b) from about 0.8 to about 3 wt. % of one or more SPF boosters including a plurality of light refracting bodies includes a styrene-acrylate copolymer composition,
   c) one or more acrylate-based polymer capable of stabilizing the composition,
   d) one or more organic UV filters,
   e) one or more thickeners;
   f) one or more film formers;
   g) one or more nonionic emulsifiers selected from the group consisting of a polyol ester, a glycerol ether, an oxyethylenated and/or oxypropylenated ether, and/or an ethylene glycol polymer, and mixture thereof; and
   wherein the composition is essentially free of oxybenzone, and
   wherein the weight percentages are based on the total weight of the oil-in-water composition.

2. The composition of claim 1, wherein the composition has an SPF of at least about 80.

3. The composition of claim 1, wherein the one or more acrylate-based polymer is a member selected from the group consisting of polyacrylate-1 crosspolymer, carbomer, acrylates/C10-30 alkyl acrylate crosspolymer, acrylates/acrylamide copolymer and acrylate copolymer, and mixture thereof.

4. The composition of claim 3, wherein the one or more acrylate-based polymer is present in an amount from about 0.1 to about 10 wt. % based on the total weight of the oil-in-water composition.

5. The composition of claim 1, wherein the one or more organic UV filters is selected from the group consisting of a para-aminobenzoic acid derivatives, ansalicylic derivatives a cinnamic derivative, a benzophenone or an aminobenzophenone, an anthranillic derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, merocyanine, an amalonitrile or malonate diphenyl butadiene derivative, a chalcone, and a mixture thereof.

6. The composition of claim 1, wherein the one or more thickeners is selected from the group C10 to C30 alkyl (meth)acrylate homopolymer, poly(behenyl acrylate) homopolymer, a poly(stearyl acrylate)homopolymer; and mixture thereof.

7. The composition of claim 1, wherein the one or more thickeners is present in an amount from about 0.1 to 10 wt. % based on the total weight of the oil-in-water composition.

8. The composition of claim 1, wherein the film former is present in an amount from about 0.1 to about 5 wt. % based on the total weight of the oil-in-water composition.

9. The composition of claim 8, wherein the film former is selected from Acrylates/Dimethicone copolymer, polyacrylate-21 (and) acrylates/dimethylaminoethylmethacrylate copolymer, polyurethanes, polysaccharides, polyvinylpyrrolidone, acrylates, and a mixture thereof.

10. The composition of claim 1, the one or more emulsifiers is a combination of glyceryl stearate and PEG-100 stearate.

11. The composition of claim 1, wherein the one or more emulsifiers is from about 0.1 to about 10 wt. % based on the total weight of the oil-in-water composition.

12. The composition of claim 1, wherein the oil-in-water composition is water resistant.

13. An oil-in-water composition comprising:
   a) from about 0.1 to about 5 wt. % of one or more antioxidants selected from diethylhexyl syringylidene malonate,
   b) from about 0.8 to about 3 wt. % of one or more SPF boosters including a plurality of light refracting bodies includes a styrene-acrylate copolymer composition,
   c) from about 0.1 to about 10 wt. % of one or more acrylates crosspolymers,
   d) from about 15 to about 40 wt. % of one or more organic UV filters,
   e) from about 0.1 to about 10 wt. % of one or more thickeners selected from the group C10 to C30 alkyl (meth)acrylate homopolymer, poly(behenyl acrylate) homopolymer, a poly(stearyl acrylate)homopolymer; and mixture thereof;
   f) from about 0.1 to about 5 wt. % of one or more film formers;
   g) from about 0.1 to about 10 wt. % of one or more nonionic emulsifiers selected from the group consisting of a polyol ester, a glycerol ether, an oxyethylenated and/or oxypropylenated ether, and/or an ethylene glycol polymer, and mixture thereof; and
   wherein the composition is essentially free of oxybenzone, and
   wherein the weight percentages are based on the total weight of the oil-in-water composition.

14. A method of protecting skin or hair from UV radiation comprising applying an effective amount of the oil-in-water formulation of claim 1 to the skin or hair.

* * * * *